(12) United States Patent
Panicker et al.

(10) Patent No.: US 7,524,639 B2
(45) Date of Patent: Apr. 28, 2009

(54) ASSAY FOR SCREENING ANTIPSYCHOTIC DRUGS

(75) Inventors: Mitradas Madhav Panicker, Bangalore (IN); Samarjit Bhattacharyya, Bangalore (IN)

(73) Assignee: Tata Institute of Fundamental Research, Maharashtra (IN)

( * ) Notice: Subject to any disclaimer, the term of this patent is extended or adjusted under 35 U.S.C. 154(b) by 0 days.

(21) Appl. No.: 11/405,061

(22) Filed: Apr. 17, 2006

(65) Prior Publication Data

US 2006/0252103 A1    Nov. 9, 2006

Related U.S. Application Data

(63) Continuation of application No. PCT/IB2004/003364, filed on Oct. 15, 2004.

(30) Foreign Application Priority Data

Oct. 17, 2003    (IN)    .......................... 840/CHE/2003

(51) Int. Cl.
  *G01N 33/567*  (2006.01)
  *G01N 33/53*   (2006.01)
  *G01N 33/542*  (2006.01)
  *G01N 33/537*  (2006.01)
  *G01N 33/566*  (2006.01)

(52) U.S. Cl. ...................... 435/7.21; 435/7.1; 435/7.72; 435/7.8; 435/7.9; 435/7.92; 436/501; 436/503

(58) Field of Classification Search ........................ None
    See application file for complete search history.

(56) References Cited

U.S. PATENT DOCUMENTS 5,891,646 A    4/1999    Barak et al.

OTHER PUBLICATIONS

Z. Lenkei et al., J Histochem Cytochem. "A highly sensitive quantitative cytosensor technique for the identification of receptor ligands in tissue extracts" Nov. 2000; 48(11):1553-64.

K. Kuwasako et al., J Biol Screen. "Visualization of the Calcitonin Receptor-like Receptor and Its Receptor Activity-modifying Proteins during Internalization and Recycling" 2000; 4(2):75-86

BR Conway et al., J Biomol Screen. "Quantification of G-Protein Coupled Receptor Internatilization Using G-Protein Coupled Receptor- Green Flourescent Protein Conjugates with the ArrayScantrade mark High-Content Screening System" 1999; 4(2):75-86—Abstract.

RN Ghosh et al., Biotechniques, "Cell-based, high-content screen for receptor internalization, recycling and intracellular trafficking" Jul. 2000; 29(1): 170-5—Abstract.

A. Bhatnagar et al., J Biol Chem. The Dynamin-dependent, Arrestin-independent Internalization of 5-Hydroxytryptamine 2A ($5\text{-}HT_{2A}$) Serotonin Receptors Reveals Differential Sorting of Arrestins and $5\text{-}HT_{2A}$ Receptors during Endocytosis Mar. 16, 2001; 276(11): 8269-77.

D.L. Willins et al., Neuroscience. Clozapine and other 5-Hydroxytryptamine-2A Receptor Antagonists Alter the Subcellular Distribution of 5-Hydroxytryptamine -2A receptors In Vitro and In Vivo 1999; 91(2): 599-606.

D.L. Willins et al., Ann NY Acad Sci. "Serotonergic Antagonist Effects on Trafficking of Serotonin $5\text{-}HT_{2A}$ Receptors in Vitro and in Vivo" Dec. 1.5, 1998; 861:127-7.

*Primary Examiner*—Olga N Chernyshev
(74) *Attorney, Agent, or Firm*—Hamre, Schumann, Mueller & Larson, P.C.

(57) ABSTRACT

A novel assay method suitable for screening of novel antipsychotics wherein the drugs may be selected based on the differential internalization of the 5-HT2A receptor in neuronal and non-neuronal cell lines effect for it to predict the extrapyramidal symptoms that may be induced by an antipsychotic without having to carry out in vivo experiments.

6 Claims, 2 Drawing Sheets

ASSAY FOR SCREENING ANTIPSYCHOTIC DRUGS

This application is a continuation of international application number PCT/IB2004/003364, filed 15 Oct. 2004.

TECHNICAL FIELD

The present invention discloses a novel assay method for the screening of antipsychotic drugs.

BACKGROUND

Serotonin (5-HT), a major neurotransmitter, with receptors distributed widely throughout the central and peripheral nervous systems, plays many physiological roles. The majority of serotonin-activated receptors belong to the superfamily of G-protein coupled receptors (GPCRs) (Bradley P B, Engel G, Feniuk W, Fozard J R, Humphrey P P, Middlemiss D N, Mylecharane E J, Richardson B P, Saxena P R (1986) Proposals for the classification and nomenclature of functional receptors for 5-hydroxytryptamine. Neuropharmacology 25:563-576; Hoyer D, Clarke D E, Fozard J R, Hartig P R, Martin G R, Mylecharane E J, Saxena P R, Humphrey P P (1994) International Union of Pharmacology classification of receptors for 5-hydroxytryptamine (Serotonin). Pharmacol Rev 46:157-203.; Baez M, Kursar J D, Helton L A, Wainscott D B, Nelson D L (1995) Molecular biology of serotonin receptors. Obes Res 3 Suppl 4:441S-447S; Saxena P R (1995) Serotonin receptors: subtypes, functional responses and therapeutic relevance. Pharmacol Ther 66:339-368; Barnes N M, Sharp T (1999) A review of central 5-HT receptors and their function. Neuropharmacology 38:1083-1152). The 5-HT2A receptor, an important serotonin receptor activates the phospholipase C-IP3 pathway Conn P J, Sanders-Bush E (1984) Selective 5HT-2 antagonists inhibit serotonin stimulated phosphatidylinositol metabolism in cerebral cortex. Neuropharmacology 23:993-996. Pauwels P J (2000) Diverse signalling by 5-hydroxytryptamine (5-HT) receptors. Biochem Pharmacol 60:1743-1750). Agonist-mediated internalization and desensitization of 5-HT2A receptors are dependent on activation of protein kinase C, but desensitization may not directly involve PKC (Berg K A, Stout B D, Maayani S, Clarke W P (2001) Differences in rapid desensitization of 5-hydroxytryptamine2A and 5-hydroxytryptamine2C receptor-mediated phospholipase C activation. J Pharmacol Exp Ther 299:593-602; Bhattacharyya S, Puri S, Miledi R, Panicker M M (2002) Internalization and recycling of 5-HT2A receptors activated by serotonin and protein kinase C-mediated mechanisms. Proc Natl Acad Sci U S A 99:14470-14475; Gray J A, Compton-Toth B A, Roth B L (2003) Identification of two serine residues essential for agonist-induced 5-HT2A receptor desensitization. Biochemistry 42:10853-10862.).

Many typical and atypical antipsychotic drugs function as antagonists at 5-HT2A receptors (Canton H, Verriele L, Millan M J (1994) Competitive antagonism of serotonin (5-HT)2C and 5-HT2A receptor-mediated phosphoinositide (PI) turnover by clozapine in the rat: a comparison to other antipsychotics. Neurosci Lett 181:65-68; Meltzer H Y (1999) The role of serotonin in antipsychotic drug action. Neuropsychopharmacology 21 Suppl 1:S106-115; Van Oekelen D, Luyten W H, Leysen J E (2003) 5-HT2A and 5-HT2C receptors and their atypical regulation properties. Life Sci 72:2429-2449). Atypical antipsychotic drugs, in general, have higher affinities for the 5-HT2A receptor than for the dopamine D2 receptor, considered their main target and have limited or no extrapyramidal side effects (Laurier C, Kennedy W, Lachaine J, Gariepy L, Tessier G (1997) Economic evaluation of zuclopenthixol acetate compared with injectable haloperidol in schizophrenic patients with acute psychosis. Clin Ther 19:316-329; Gerlach J (2002) Improving outcome in schizophrenia: the potential importance of EPS and neuroleptic dysphoria. Ann Clin Psychiatry 14:47-57; Marder S R, McQuade R D, Stock E, Kaplita S, Marcus R, Safferman A Z, Saha A, Ali M, Iwamoto T (2003) Aripiprazole in the treatment of schizophrenia: safety and tolerability in short-term, placebo-controlled trials. Schizophr Res 61:123-136). In general assays have concentrated on determining the binding affinities of drugs to 5-HT2A receptors in order to study the possible clinical use of these drugs. Like serotonin, many atypical antipsychotics, viz., clozapine, olanzapine etc. but not typical antipsychotics e.g. haloperidol though antagonists, cause internalization of 5-HT2A receptors both in vitro and a redistribution of the receptor in vivo but the mechanism of internalization and subsequent events remain unknown (Willins D L, Berry S A, Alsayegh L, Backstrom J R, Sanders-Bush E, Friedman L, Roth B L (1999) Clozapine and other 5-hydroxytryptamine-2A receptor antagonists alter the subcellular distribution of 5-hydroxytryptamine-2A receptors in vitro and in vivo. Neuroscience 91:599-606). The authors stated that the altered sub-cellular distribution of 5-HT2A receptors within neurons may be related to the therapeutic effects of the atypical antipsychotics. They could not conclude whether the redistribution of the receptor in the dendrites of neurons observed in vivo were the result of internalization or due to a blockage of the transport of newly-synthesized receptors or reduced synthesis. These authors had tested 7 drugs (which would have caused different levels of EPS) and had also not reported any correlation between internalization levels and extrapyramidal symptoms. These experiments had used antibodies against the 5-HT2A receptor to determine internalization.

A typical antipsychotic drugs viz., clozapine, olanzapine etc., show negligible levels of extrapyramidal side effects; drugs such as chlorpromazine show moderate levels of extrapyramidal side effects while typical antipsychotic drugs viz., haloperidol or fluphenazine, cause severe extrapyramidal side effects (Baldessarini, R. J., and Tarazi, F. I. (2001) in *Goodman & Gilman's The Pharmacological Basis of Therapeutics* (Hardman, J. G., Limbird, L. E., and Goodman Gilman, A., eds), Tenth Ed., pp. 485-520, McGraw-Hill Companies, Inc, USA). Currently there are no available in vitro assays available to screen antipsychotic drugs for extrapyramidal side effects. In vivo assays are essential to determine these effects. It would be therefore useful to develop novel assays that can rapidly provide more on the effect of the drug on the receptor than binding and potentially predict in vivo effects from in vitro assays. Internalization of the receptor, second messenger generation etc. could be suitable but as of now no data exists to provide such predictions.

Internalization of receptors in cell lines have been determined using antibodies directed against various portions of the receptor or by providing fluorescent ligands that induce internalization or by tagging the receptor with a fluorescent protein such as the green fluorescent protein i.e. GFP or a small epitope for which antibodies or ligands are available (Barak L S, Zhang J, Ferguson S S, Laporte S A, Caron M G (1999) Signaling, desensitization, and trafficking of G protein-coupled receptors revealed by green fluorescent protein conjugates. Methods Enzymol 302:153-171). We and others have shown that GFP can be attached to the cytoplasmic tail of the 5-HT2A receptor and the receptor-GFP fusion protein is functional (Bhatnagar A, Willins D L, Gray J A, Woods J, Benovic J L, Roth B L (2001) The dynamin-dependent, arrestin-independent internalization of 5-hydroxytryptamine 2A (5-HT2A) serotonin receptors reveals differential sorting of arrestins and 5-HT2A receptors during endocytosis. J Biol Chem 276:8269-8277; Bhattacharyya S, Puri S, Miledi R, Panicker M M (2002) Internalization and recycling of 5-HT2A receptors activated by serotonin and protein kinase C-mediated mechanisms. Proc Natl Acad Sci U S A 99:14470-14475).

Current pharmacological assays use the binding of and either the activation or inhibition of the receptor to determine the effects of various drugs and internalization has not been suggested as a significant indicator for efficacy of the drug or as a reason for side effects often seen. Interestingly, we and others have observed that a number of antagonists cause internalization (Willins D L, Berry S A, Alsayegh L, Backstrom J R, Sanders-Bush E, Friedman L, Roth B L (1999) Clozapine and other 5-hydroxytryptamine-2A receptor antagonists alter the subcellular distribution of 5-hydroxytryptamine-2A receptors in vitro and in vivo. Neuroscience 91:599-60). What we have determined in addition is that for a number of antipsychotics—both typical and atypical their side effects in particular the extrapyramidal symptoms could be directly correlated to its effect on the internalization of the receptor. We also observed that the internalization is also dependent on the cell line used i.e. whether it is a neural or non-neural cell line. Such an assay to classify various antagonists has not been proposed before. We are of the opinion that the effects of drugs on the internalization of the receptor would be a significant and very useful assay to rationally screen for and predict the effectiveness of drugs. Similar assays can also be designed for a large number of receptors that bind to other ligands and should prove extremely useful. Similar receptors can be expressed in non-neuronal and neuronal cells and used to study the internalization of the receptor in these cell lines on application of various ligands. The internalization of the receptor can be determined through fluorescence microscopy. In case of the EGFP the fluorescence can be directly visualized and in case of the Myc-tagged receptor, a monoclonal antibody directed against the Myc epitope is used. Either this antibody or another antibody directed against the Myc antibody is labeled with a fluorophore and used. This assay is used to screen antipsychotics for their ability to cause internalization of the receptor in cells. The ability of the antipsychotic to internalize negatively correlates with the extrapyramidal symptoms the drug causes in vivo.

SUMMARY OF INVENTION

The mammalian 5-HT2A receptor like many of the seven transmembrane receptors has an extracellular N-terminus and an in intracellular C-terminus. The present invention is the construction and use of the full-length wild type rat 5-HT2A receptor fused to the enhanced Green fluorescent (EGFP) at the C terminal intracellular end of the receptor as well as the construction of the full length wild type rat 5-HT2A receptor fused to the Myc epitope recognized by the mouse monoclonal antibody 9E10—the 9E10 antibody epitope derives from a protein sequence in the human proto-oncogene p62(c-myc) and is widely used as a protein fusion tag, at the extracellular N terminus of the receptor (Hilpert K, Hansen G, Wessner H, Kuttner G, Welfle K, Seifert M, Hohne W. (2001) Anti-c-myc antibody 9E10: epitope key positions and variability characterized using peptide spot synthesis on cellulose. Protein Eng. 10:803-6). Cells that permanently or transiently express the 5-HT2A-EGFP or the 5-HT2A receptor with the Myc epitope tagged to the extracellular N-terminus of the receptor are used as an example. We have shown that these modified 5HTA receptors are functional in cell lines and have developed functional assays for both receptor constructs to determine the effects on extracellular application of ligands e.g. agonists, antagonists etc. These modified receptors allow for easy and quick determinations of functional activity and their effect on the intracellular distribution of these receptors in the presence of ligands. Both of these modified receptors in cell lines can be used in high throughput assays to determine if:

1. A given ligand causes activation of the receptor by measuring increase in Ca ion levels within the cell.
2. If the ligand causes internalization of the receptor and the rate of the internalization process.
3. Comparison of the levels and distribution of the internalized receptor within the cell.
4. The specific biochemical pathways that are involved in the process of internalization using inhibitors specific to the pathways concerned.
5. Internalized receptors recycle back to the surface or are degraded and the rate of the recycling process and the pathways that are involved.

The internalization of the receptor is measured by either determining the localization of the green fluorescent protein tag fused to the receptor or the myc tag that has been fused to the N-terminus of the receptor. The former can be easily observed due to its native fluorescence and the internalization of the latter can be determined using fluorescent primary or secondary antibodies directed against the N terminus-myc epitope tag.

DESCRIPTION OF FIGURES

With reference to the accompanying FIGS. 1 and 2, it was found that the typical antipsychotic drug, haloperidol (10 μM) did not induce any observable internalization of the receptor in either SB1 or N1E-115 cells i.e. it induced a Type C pattern (FIG. 1C, D), whereas the typical antipsychotic drug chlorpromazine (10 μM) did not induce any observable internalization of the receptor in SB1 cells (Type C) but induced internalization of the receptor as seen by almost complete disappearance of fluorescence from the distal segments of neurites in N1E-115 cells along with the appearance of fluorescence in recycling endosomal compartments i.e. aType B pattern (FIG. 1E, F). Atypical antipsychotic drugs also showed differential effects on internalization of the receptor in neuronal and non-neuronal cells. The atypical antipsychotic drug risperidone (10 μM) caused a punctate pattern of internalization of the receptor in SB1 cells in 10 min but induced a pattern of internalization similar to that induced by chlorpromazine (Type B) in N1E-115 cells (FIG. 1G, H). Other atypical antipsychotics, for example, 10 μM clozapine caused the Type A pattern of internalization of the receptor in both SB1 cells and N1E-115 cells i.e. almost complete disappearance of the fluorescence from neurites and strong fluorescence in the recycling endosomal compartment (FIG. 1I, J). These conclusions have been drawn from multiple experiments (N=3) in which at least 100 to 150 cells were scored for the pattern of internalization. In all cases a minimum of 90 to 95% of the cells exhibited the scored pattern. In case of N1E-115, where transiently transfected cells were used, cells exhibiting too intense fluorescence were not included in the analysis.

DETAILED DESCRIPTION OF INVENTION

Figure 1:
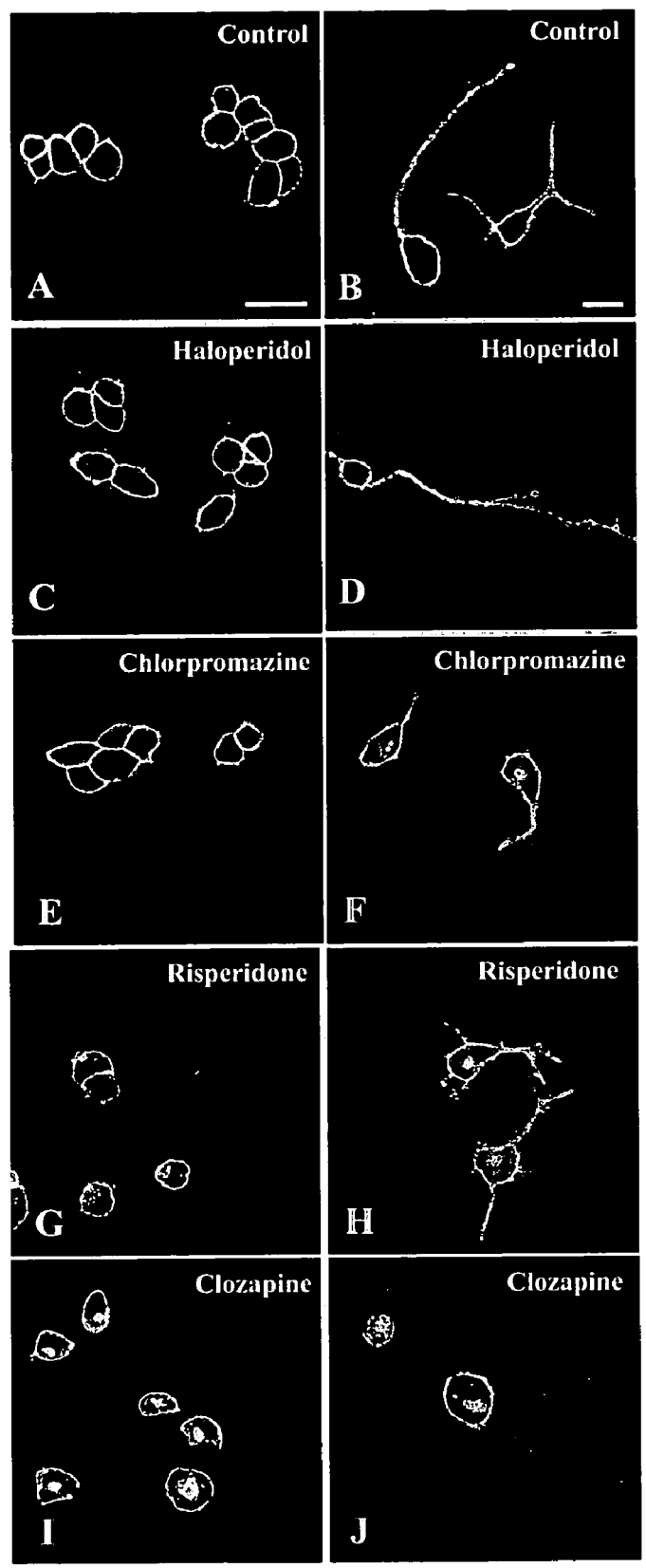
Figure 2:
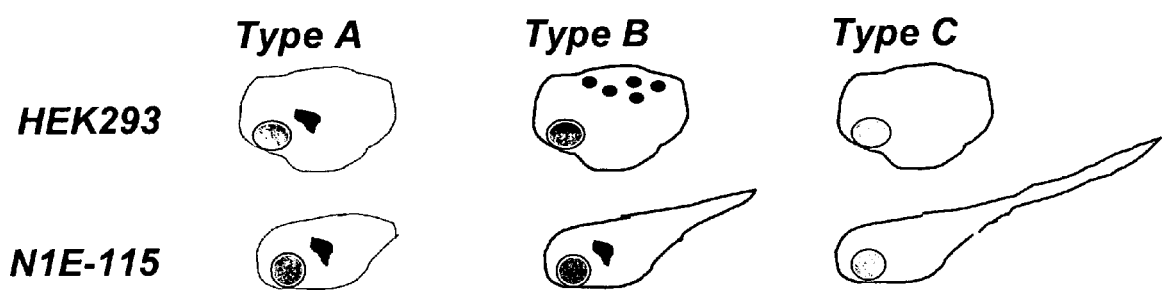

The instant invention discloses a method for the determination of drug activity comprising binding with receptors without activation or inhibition.

The drug activity is determined by differential internalization of neuronal and non-neuronal cell lines.

The differential internalization leads to extrapyramidal symptoms. The term "extrapyramidal symtoms" or "EPS" described herein also means "extrapyramidal side effects", and encompasses the same symptoms as "extrapyramidal side effects."

The differential internalization of the receptor is measured by either determining the localization of fluorescent protein tag fused to the receptor or the myc tag that has been fused to the N-terminus of the receptor.

The drug is an antipsychotic drug.

The antipsychotic drug is selected from clozapine, quitapine, olanzapine, aripiprazole, risperidone, loxapine, ziprasidone, chlorpromazine, zuclopenthixol, fluphenazine and haloperidol. The assay can be used to identify antipsychotic properties of other compounds.

The drug activity is used as an assay method.

The assay is a high throughput assay.

The drug activity is used for screening.

The screening is a high throughput screening.

The drug activity determination is further used to develop a kit.

The following examples further illustrate the invention, it being understood that the invention is not intended to be limited by the details disclosed therein.

Materials pSR2 plasmid, with the rat 5-HT2A receptor full-length cDNA construct, was a generous gift from David Julius (University of California, San Francisco).

pEGFP-N1 vector was from Clontech, USA. pCruz-Myc vector was from Santa Cruz Biotechnology, USA.

DMEM, penicillin, streptomycin, lipofectamine, G418, OptiMEM, dNTPs, Hanks balanced salt solution (HBSS) and AB-AM (antibiotic-antimycotic) mix were obtained from Life Technologies, USA.

ScaI, BglII, BamHI, EcoRI, Vent polymerase and T4 DNA ligase were purchased from New England Biolabs, USA.

Rhod2-AM dye and pluronic were from Molecular probes, USA.

FBS, poly-DL-Ornithine, serotonin (5-HT), clozapine, risperidone, chlorpromazine, haloperidol, cycloheximide, sphingosine, calphostin C were purchased from Sigma, USA.

Other drugs were obtained as tablets from the pharmacy and extracted in DMSO.

N1E-115 cell line was from ATCC, USA.

Anti-Myc monoclonal antibody was from the culture supernatant of the clone called, 9E10 obtained from Santacruz Biotechnology (USA).

Anti-Myc monoclonal antibody conjugated to FITC was also obtained from Santacruz Biotechnology (USA).

Anti-GFP monoclonal antibody was from Bangalore Genei (India).

Tissue culture plastic wares were from Nalge Nunc International, Denmark.

Coverslips (Gold seal cover glass, No. 1) were from Clay Adams, USA.

5-HT solution: To make 10 mM 5-HT solution, 3.87 mg of 5-hydroxytryptamine creatinine sulfate complex was added to 800 μl of double-distilled autoclaved water and concentrated HCl was added dropwise until the crystal dissolved. The volume was made upto 1 ml with double-distilled autoclaved water.

DMEM: Dulbecco's Modified Eagle medium (DMEM) and 3.7 g of sodium bicarbonate were dissolved in 800 ml of double-distilled autoclaved water. Penicillin (10 IU/ml) and streptomycin (10 μμg/ml) were added in it. The volume was made upto 1 litre with double-distilled autoclaved water. The medium was filter-sterilized under vacuum through a 0.45 μm filter.

10% DMEM: 10% fetal bovine serum (FBS) in DMEM.

DMEM to culture N1E-115 cell line (N1E-DMEM): Dulbecco's Modified Eagle Medium (DMEM) and 1.5 g sodium bicarbonate were dissolved in 1 litre of double-distilled autoclaved water. The medium was filter-sterilized under vacuum through a 0.45 μm filter.

10% N1E-DMEM: 10% fetal bovine serum (FBS), 1× AB-AM (antibiotic-antimycotic) mix in N1E-DMEM.

10× phosphate buffered saline (PBS): 80 g NaCl, 2 g KCl, 14.4 g $Na_2HPO_4$ and 2.4 g $KH_2PO_4$ were dissolved in 800 ml of double-distilled water. The pH was adjusted to 7.4 and the volume was made upto 1 litre with water and sterilized by autoclaving.

1× Puck's D1 solution: 5.50 mM Glucose, 5.40 mM KCl, 58.40 mM Sucrose, 17.00 mM $Na_2HPO_4$, 138.00 mM NaCl and 0.22 mM $KH_2PO_4$ were dissolved in double-distilled water. The solution was then filter-sterilized by using a 0.22 μm filter.

20% paraformaldehyde (PFA): 20 g paraformaldehyde was dissolved in 100 ml of 0.1 M phosphate buffer (pH-7.3) (20 mM $NaH_2PO_4$+80 mM $Na_2HPO_4$) at 60° C. The solution was aliquoted into 1.5 ml micro-centrifuge tubes and stored at −20° C.

Ascorbate buffer: Sodium ascorbate, ascorbic acid, $CaCl_2$ and $MgCl_2$ were dissolved in double-distilled water to obtain a final concentration of 140 mM sodium ascorbate, 65 mM ascorbic acid, 1 mM $CaCl_2$ and 1 mM $MgCl_2$. The pH of the ascorbate buffer was 4.5.

EXAMPLE 1

Generation of SR2-GFP receptor and HEK293 cells stably expressing SR2-GFP receptors: Enhanced green fluorescence protein (EGFP) had been tagged at the C-terminus of the full-length rat 5-HT2A receptor (SR2-GFP) and a stable line, SB-1, expressing fluorescent SR2-GFP receptors was established in the HEK293 cell line. The 1.8 kb cDNA fragment containing the entire rat $5-HT_{2A}$ receptor-coding region was obtained from the plasmid pSR2 by PCR using two primers. The forward primer contained the EcoR1 site and the coding sequence of the first few amino acids encoding the receptor. The reverse primer contained the non-coding strand sequence of the last few amino acids of the receptor followed by a BamH1 site which when cut and cloned into the EcoR1 BamH1 double-digested pEGFP-N1 vector from Clontech, USA resulted in the coding region of the receptor being in frame with the EGFP coding region. The entire segment that was cloned into the vector was sequenced to ensure that mutations in the coding region were absent and that the receptor coding region was in frame with the EGFP coding region. The receptor-EGFP fusion protein can be expressed in eukaryotic cells from a CMV promoter present in the pEGFP- N1 vector. The vector also has a selectable marker i.e. neomycin for stable integration and expression in eukaryotic cells.

EXAMPLE 2

Generation of HEK293 cell lines with stable expression of SR2-GFP: HEK293 cells were maintained in Dulbecco's Modified Eagle medium (DMEM) supplemented with 10% fetal calf serum, penicillin (100 IU/ml) and streptomycin (100µg/ml) at 37° C., 5% $CO_2$. Cells were grown to 65-70% confluency in 35 mm dishes and transfected with 2 µg of SR2-GFP DNA using 10 µg of lipofectamine in 1 ml Opti-MEM. After 2 days in culture, cells were selected with 1 mg/ml of the neomycin analogue G418 and 30 stable lines (SB series) expressing varying amounts of SR2-GFP receptors, as determined through fluorescence expression, were established. All further experiments were conducted with two of these lines—SB-1 and SB-2, which expressed high and medium levels of the fusion receptor, respectively.

EXAMPLE 3

Construction of the Myc $5-HT_{2A}$ fusion receptor: To tag Myc at the N-terminus of the full-length rat $5-HT_{2A}$ receptor, the entire rat $5-HT_{2A}$ coding region was obtained by PCR using SR2-GFP DNA as the template. The upper primer contained the ScaI restriction enzyme site and the lower primer had the stop codon and the BglII restriction enzyme site. The PCR product was then digested with ScaI and BglII restriction enzymes. To clone this insert into the pCruz-MycA vector obtained from Santa Cruz, USA. pCruz-MycA plasmid DNA was digested with the ScaI and BglII restriction enzymes. The digested PCR product was then ligated into the digested vector DNA using the E. coli T4 DNA ligase. The ligated mix was then transformed in DH5α competent cells using kanamycin as the selection antibiotic. Plasmid DNA was isolated from individual colonies and presence of the insert was confirmed by restriction enzyme digestion. The entire cloned region was then sequenced to ensure that the Myc-$5-HT_{2A}$ receptor fusion was in frame and there were no mutations in the coding region of the receptor.

EXAMPLE 4

Transient Transfection: To obtain cells transiently expressing the receptor i.e. neuronal or non-neuronal cell lines e.g. N1E-115 cells and HEK 293 cells respectively, with plasmid DNA, cells were grown to 65-70% confluency in 35 mm dishes or 35 mm coverslip dishes coated with 20 µg/ml poly-DL-ornithine. Transfection was done with 2 µg of CsCl purified DNA complexed with 10 µg of lipofectamine in 1 ml OptiMEM to obtain high efficiency transfection. Expression was observed 24-36 hrs after transfection. These cells were then used for the assays.

EXAMPLE 5

For cells permanently or transiently expressing the GFP-tagged receptor (Method I): Non-neuronal cell line—HEK 293 cells as an example: Cells that permanently or transiently express the $5-HT_{2A}$-EGFP in HEK 293 cells are used. The cell line SB1 (described in the materials section is an example of a cell line permanently expressing the GFP-tagged fluorescent receptor) is an example. Cells that are transiently transfected with the appropriate plasmid construct may be used provided receptor expression is adequate which may be measured by the level of fluorescent receptor expressed using a fluorescence microscope with appropriate filters. The cells are grown on glass cover slips dishes coated with polylysine or polyornithine (coated for 1 hour with 100 micrograms/ml of either polylysine or polyornithine in water or PBS). Tissue culture grade plastic dishes of various formats that are commercially available may also be used depending on the magnification desired and the type of microscope objectives available.

In order to study internalization of the $5-HT_{2A}$ receptor in SB1 cells, cells were plated onto poly-DL-ornithine (20 µg/ml)—coated coverslip dishes and grown to 60-70% confluency. After 24 hrs in culture, cells were washed twice with serum free-DMEM to remove endogenous 5-HT present in serum. Protein synthesis was then blocked with cycloheximide at 100 µg/ml for 5 hrs to eliminate fluorescence from receptors being synthesized and present in the Golgi. After 5 hrs, the fluorescence was observed only at the cell surface. The cells may also be alternatively grown in 1% serum containing media to decrease protein synthesis for 48 hours or a time period determined to be adequate for clearing internal fluorescence dependent on the cell line and growth conditions adopted. Antipsychotics or an agonist such as serotonin (i.e. positive control) at the desired concentrations in DMEM were then applied for 10 mins. At the end of this period, cells were fixed in 4% paraformaldehyde in phosphate buffered saline (PBS) for 30 min, washed with PBS and imaged using a confocal microscope as described below.

A laser-scanning confocal microscope (Model MRC1024—BioRad) attached to a Nikon inverted microscope (Nikon eclipse TE300) and Lasersharp acquisition software were used in this case. A 60× oil immersion objective (NA=1.4) and 20× objective (NA=0.75) were used with laser power at 30% in all studies. GFP excitation/emission was achieved with a filter set (488 nm/510 nm) designed for fluorescein detection. Images were processed with Adobe Photoshop software using identical values for contrast and brightness. Typically 100-150 cells were randomly chosen and imaged in any one experiment and all experiments were repeated at least three times. In all experiments, cycloheximide was present until the cells were fixed. The number of cells that show internalized fluorescence and the pattern of fluoresence were estimated. Live, unfixed cells may also be imaged if the equipment permits live cell imaging.

Neuronal Line—N1E-115 as an example. This example also serves for a transiently transfected cell line: N1E-115 cells were cultured in N1E—DMEM (without sodium pyruvate) supplemented with 10% fetal bovine serum, 1×AB-AM (antibiotic—antimycotic) mix. Cells were passaged using Puck's D1 solution (as described before).

To study internalization of the $5-HT_{2A}$ receptor in N1E-115 cells, undifferentiated N1E-115 cells grown on cover slip dishes cells were plated onto poly-DL-ornithine (20 µg/ml)—coated coverslip dishes and grown to 60-70% confluency. These cells were transfected with 2 µg of the SR2-GFP DNA mixed with 10 µg of lipofectamine in 1 ml OptiMEM media. 24 hrs after transfection, differentiation medium (1% DMSO+1% FBS+1% AB-AM mix in DMEM) was added in place of 10% DMEM. After 3 days, differentiated cells formed long neurites. Experiments were then performed using the same protocol as described for SB1 cells above.

EXAMPLE 6

Using antibodies directed against the receptor (Method II): The internalization may be measured using antibodies directed against the portions of the receptor or against an epitope tagged to the receptor e.g. the Myc epitope. In case of cells expressing the Myc or a similar epitope tagged to the extracellular portion of the receptor, the internalization can be measured using the "antibody-feeding method" outlined below. The primary antibody may also be directed to the N-terminal extracellular portion of the receptor or any other extracellular portion of the receptor that will not interfere with the binding of ligands to the receptor being assayed or prevent the internalization of the receptor in the assay. The primary antibody used may be tagged with a fluoropore or a fluorophore-tagged antibody directed against the primary antibody may be used. In case the epitope is intracellular or extracellular then standard immunocytochemical methods may also be employed to localize the receptor. The process is detailed below.

A. Antibody Feeding Method—Myc Tagged 5-HT2A Receptor:

In this example we have used the Myc tagged rat 5-HT2A receptor the construction of which is detailed in the materials section. The Myc tag is exhibited on the extracellular surface. Briefly, HEK293 cells were transfected with the Myc 5-HT$_{2A}$ receptor using the transfection protocol as described above. 36 hrs after transfection, cells were washed twice with DMEM. Subsequently, cells were incubated in 10% bovine serum albumin (BSA) in DMEM for 30 min to prevent the non-specific binding. Cells were then washed thrice with DMEM and incubated in the anti-Myc monoclonal antibody conjugated to FITC at 1:20 dilution from (SantaCruz Biotechnology, USA) for 2 hrs at room temperature. After that, cells were washed thrice with DMEM and various ligands at the desired concentrations to be assayed were applied in DMEM for 10 min. The cells were then fixed in methanol for 5 min at −20° C., washed thrice in PBS and imaged using a confocal microscope as detailed before.

In case of the Myc epitope, the anti-Myc monoclonal antibody was from the culture supernatant of the clone called, 9E10 obtained from Santacruz Biotechnology (USA). The anti-Myc monoclonal antibody conjugated to FITC was also obtained from Santacruz Biotechnology (USA). Any transiently transfectable cell line may be used. A cell line permanently expressing the tagged receptor may be used. The primary antibody may also be directed to the N-terminal extracellular portion of the receptor or any other extracellular portion of the receptor that will not interfere with the binding of ligands to the receptor being assayed or prevent the internalization of the receptor in the assay.

B. Standard Immunocytochemical Protocol:

If antibodies are only available only against the intracellular portions of the receptor or if binding of the antibody prevents the internalization then the assay is modified as follows. The cells expressing the receptor either transiently or permanently are treated with cycloheximide as detailed above. The ligands are added at the appropriate concentration and after the desired period of incubation the cells are fixed in 4% paraformaldehyde as described before. The fixation protocol may be appropriately modified depending on the instructions supplied with the primary and secondary antibodies. The receptors in the fixed cells are localized by fluorescence immunocytochemistry using antibodies directed against the receptor as the primary antibody. The concentrations of the antibody used will be determined by the supplier's instructions. The primary antibody may have a fluorophore attached or an antibody directed against the primary antibody may be used with an appropriate fluorophore attached.

Examples of Results from the Assay Described:

It has been reported that some antipsychotics, which function as antagonists or inverse agonists, cause 5-HT$_{2A}$ receptors to internalize (Willins et. al., 1999). Indeed many typical and all the atypical antipsychotic drugs that we have tested caused the internalization of the rat 5-HT$_{2A}$ receptor tagged with EGFP in SB1 and N1E-115 cells without activating the receptor. Surprisingly, the pattern of internalization seen was not uniform and was characteristic of the antipsychotic and the cell line used. We have classified the pattern of internalization as i.) Type A—highly fluorescent typical recycling endosome in SB1 non-neuronal cells and near complete loss of fluorescence in the neurites of N1E-115 neuronal cells with most of the fluorescence present in the recycling endosomal compartment in the soma, ii) Type B—presence of some intracellular punctate fluorescence but no typical recycling endosomal fluorescence in SB1 non-neuronal cells and disappearance of fluorescence from the distal segments of neurites with appearance of internal fluorescence in the soma of N1E-115 neuronal cells and iii) Type C—no visible internalization of fluorescence i.e. the receptor in either the non-neuronal SB-1 1 or neuronal N1E-115 cells. The patterns of internalization by various typical and atypical antipsychotics in both cell lines are shown in Table 1 and the pattern is depicted in a cartoon below Table 1. Interestingly, the patterns of internalization of the receptor showed strong correlation with extrapyramidal side effects (EPS) associated with the drug, especially in neuronal N1E-115 cells as depicted in Table 1. The EPS values are obtained from a standard reference (Baldessarini, R. J., and Tarazi, F. I. (2001) in *Goodman & Gilman's The Pharmacological Basis of Therapeutics* (Hardman, J. G., Limbird, L. E., and Goodman Gilman, A., eds), Tenth Ed., pp. 485-520, McGraw-Hill Companies, Inc, USA) or obtained from other published medical sources.

TABLE I

Pattern of Internalization with atypical and typical Antipsychotic Drugs

| | | Receptor internalization | | |
| --- | --- | --- | --- | --- |
| | Antipsychotics Drugs | SB1 cells | N1E-115 cells | Extrapyramidal side effects (EPS) |
| Atypical antipsychotic drugs | Clozapine | Type A | Type A | Very low |
| | Quitapine | Type A | Type A | Very low |
| | Olanzapine | Type A | Type A | Very low |
| | Aripiprazole | Type A | Type A | Very low |
| | Risperidone | Type B | Type B | Moderate |
| | Loxapine | Type B | Type B | Moderate |
| | Ziprasidone | Type B | Type B | Moderate |
| Typical antipsychotic drugs | Chlorpromazine | Type C | Type B | Moderate |
| | Zuclopenthixol | Type C | Type B | Moderate |
| | Fluphenazine | Type C | Type C | Very high |
| | Haloperidol | Type C | Type C | Very high |

The invention claimed is:

1. A method for the ex vivo determination of a level of severity of extrapyramidal symptoms caused by a compound in a subject, the compound having unknown extrapyramidal side effects in the subject to be treated with the compound, the method comprising:
   (a) applying the compound to a non-neuronal cell line that expresses a 5-HT$_{2A}$ receptor;
   (b) determining a pattern of differential internalization of the receptor in the cell line, wherein the pattern of internalization is classified into:
      (i) Type A, which exhibits internalization of the receptor to a recycling endosome in the cell line and loss of the receptor from a cell surface with the internalized receptor being localized to the recycling endosome;

(ii) Type B, which exhibits internalization of the receptor to the recycling endosome in the cell line and loss of the receptor from the cell surface along with appearance of the receptor in puncta within the cell line; and (iii) Type C, which exhibits no visible internalization of the receptor in the cell line, such that Type A predicts low extrapyramidal symptoms, Type B predicts moderate extrapyramidal symptoms and Type C predicts high extrapyramidal symptoms, wherein the compound is an antipsychotic drug.

2. A method as claimed in claim 1, wherein the pattern of internalization is visualized using a fluorescent protein tag fused to the receptor.

3. A method as claimed in claim 1, wherein said pattern of internalization visualized using myc tag fused to an N-terminus of said receptor.

4. A method for the ex vivo determination of a level of severity of extrapyramidal symptoms caused by a compound in a subject, the compound having unknown extrapyramidal side effects in the subject to be treated with the compound, the method comprising:

(a) applying the compound to a neuronal cell line that expresses a $5\text{-}HT_{2A}$ receptor;

(b) determining a pattern of differential internalization of the receptor in the cell line, wherein the pattern of internalization is classified into:

(i) Type A, which exhibits internalization of the receptor to a recycling endosome in the cell line and loss of the receptor from a cell surface with the internalized receptor being localized to the recycling endosome;

(ii) Type B, which exhibits internalization of the receptor to the recycling endosome in the cell line and loss of the receptor from the cell surface along with appearance of the receptor in puncta within the cell line; and (iii) Type C, which exhibits no visible internalization of the receptor in the cell line, such that Type A predicts low extrapyramidal symptoms, Type B predicts moderate extrapyramidal symptoms and Type C predicts high extrapyramidal symptoms, wherein the compound is an antipsychotic.

5. A method as claimed in claim 4, wherein the pattern of internalization is visualized using a fluorescent protein tag fused to the receptor.

6. A method as claimed in claim 4, wherein said pattern of internalization is visualized using a myc tag fused to an N terminus of the receptor.

* * * * *